(12) United States Patent
Kamenoue et al.

(10) Patent No.: US 11,739,039 B2
(45) Date of Patent: *Aug. 29, 2023

(54) SURFACTANT AND SURFACTANT COMPOSITION

(71) Applicant: KAO CORPORATION, Tokyo (JP)

(72) Inventors: Shogo Kamenoue, Wakayama (JP); Hiroshi Hori, Wakayama (JP); Takashi Wakasa, Wakayama (JP); Shunsuke Koriki, Wakayama (JP); Takashi Mizooku, Tokyo (JP); Ryuya Arata, Wakayama (JP); Akiyoshi Kimura, Wakayama (JP)

(73) Assignee: KAO CORPORATION, Tokyo (JP)

( * ) Notice: Subject to any disclaimer, the term of this patent is extended or adjusted under 35 U.S.C. 154(b) by 63 days.

This patent is subject to a terminal disclaimer.

(21) Appl. No.: 17/605,740

(22) PCT Filed: May 28, 2020

(86) PCT No.: PCT/JP2020/021211
§ 371 (c)(1),
(2) Date: Oct. 22, 2021

(87) PCT Pub. No.: WO2020/241786
PCT Pub. Date: Dec. 3, 2020

(65) Prior Publication Data
US 2022/0213017 A1    Jul. 7, 2022

(30) Foreign Application Priority Data

May 28, 2019 (JP) ............................... 2019-099445
May 28, 2019 (JP) ............................... 2019-099462
Mar. 11, 2020 (JP) ............................... 2020-042327

(51) Int. Cl.
*C07C 43/13* (2006.01)
*C09K 8/584* (2006.01)

(52) U.S. Cl.
CPC .............. *C07C 43/13* (2013.01); *C09K 8/584* (2013.01)

(58) Field of Classification Search
CPC ........... C07C 43/13; C07C 1/24; C07C 41/03; C09K 8/584; C09K 8/602; C07D 301/12; C07D 303/04; C10M 129/08; C10M 169/04; C10M 129/16; C10M 2203/1025; C10M 2207/04; C10N 2030/06; C10N 2040/25; C10N 2040/04
USPC ................................ 508/583, 577; 166/270.1
See application file for complete search history.

(56) References Cited

U.S. PATENT DOCUMENTS

| | | | |
|---|---|---|---|
| 3,639,240 A | 2/1972 | Mutchler | |
| 4,719,084 A | 1/1988 | Schmid et al. | |
| 5,429,820 A | 7/1995 | Kamitani et al. | |
| 5,614,268 A | 3/1997 | Varley et al. | |
| 6,387,867 B1 | 5/2002 | Ishikawa et al. | |
| 9,296,942 B2 | 3/2016 | Weerasooriya et al. | |
| 10,045,529 B2 | 8/2018 | Griese et al. | |
| 2001/0012821 A1 | 8/2001 | Koishikawa et al. | |
| 2002/0025295 A1 | 2/2002 | Kim | |
| 2004/0266647 A1 | 12/2004 | Kubo et al. | |
| 2005/0037931 A1 | 2/2005 | Rowland et al. | |
| 2007/0155635 A1 | 7/2007 | Tagawa et al. | |
| 2010/0222603 A1 | 9/2010 | Selifonov | |
| 2010/0274039 A1 | 10/2010 | Choi et al. | |
| 2014/0298577 A1 | 10/2014 | Burt et al. | |
| 2015/0005225 A1 | 1/2015 | Tulchinsky et al. | |

(Continued)

FOREIGN PATENT DOCUMENTS

| | | |
|---|---|---|
| CN | 1826400 A | 8/2006 |
| CN | 101412566 A | 4/2009 |
| CN | 101909744 A | 12/2010 |
| CN | 104350137 A | 2/2015 |
| CN | 107313271 A | 11/2017 |
| JP | 53-137905 A | 12/1978 |

(Continued)

OTHER PUBLICATIONS

English translation of the Chinese Search Report for Chinese Application No. 202080032131.1, dated Aug. 23, 2022.

(Continued)

*Primary Examiner* — Prem C Singh
*Assistant Examiner* — Francis C Campanell
(74) *Attorney, Agent, or Firm* — Birch, Stewart, Kolasch & Birch, LLP

(57) ABSTRACT

The present invention provides: a surfactant that has outstanding emulsifiability in oil, wetting properties with respect to matter, osmotic properties with respect to fiber products, and washability; and a surfactant composition that contains the surfactant. This surfactant contains at least one compound represented by a Chemical Formula (1).

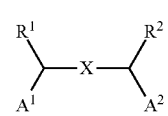

[Chemical Formula (1)]

(In the formula: $R^1$ is a hydrogen atom or an aliphatic hydrocarbon group with a carbon number of 1-33; $R^2$ is an aliphatic hydrocarbon group with a carbon number of 1-33; the total carbon number of $R^1$ and $R^2$ is 1-34; X is a single bond or an aliphatic hydrocarbon group with a carbon number of 1-5; either $A^1$ or $A^2$ is —OH; and the other is —O—$CH_2$—CH(OH)—$CH_2$OH or —O—CH(—$CH_2$—OH)$_2$.)

20 Claims, No Drawings

(56) References Cited

U.S. PATENT DOCUMENTS

| | | | |
|---|---|---|---|
| 2015/0133353 A1 | 5/2015 | Arai et al. | |
| 2015/0191672 A1 | 7/2015 | Hanyuda et al. | |
| 2016/0100574 A1 | 4/2016 | Pesaro et al. | |
| 2018/0371362 A1 | 12/2018 | Keuleers et al. | |
| 2022/0144741 A1* | 5/2022 | Kamenoue | C09D 5/00 |
| 2022/0177801 A1* | 6/2022 | Kamenoue | C10M 129/08 |
| 2022/0213383 A1* | 7/2022 | Kamenoue | C23F 11/12 |
| 2022/0220363 A1* | 7/2022 | Kamenoue | C07C 41/03 |

FOREIGN PATENT DOCUMENTS

| | | |
|---|---|---|
| JP | 55-105632 A | 8/1980 |
| JP | 62-235487 A | 10/1987 |
| JP | 5-984 A | 1/1993 |
| JP | 2002-235093 A | 8/2002 |
| JP | 2007-146029 A | 6/2007 |
| JP | 2008-506810 A | 3/2008 |
| JP | 2010-260917 A | 11/2010 |
| JP | 2012-506895 A | 3/2012 |
| JP | 2014-25040 A | 2/2014 |
| JP | 2015-501363 A | 1/2015 |
| JP | 2015-124392 A | 7/2015 |
| JP | 2016-56111 A | 4/2016 |
| JP | 2016-148095 A | 8/2016 |
| JP | 2017-197732 A | 11/2017 |
| JP | 2018-104752 A | 7/2018 |
| JP | 2018-172620 A | 11/2018 |
| JP | 2019-6998 A | 1/2019 |
| KR | 2001-0111811 A | 12/2001 |
| WO | WO 00/43479 A1 | 7/2000 |
| WO | WO 2005/018300 A2 | 3/2005 |
| WO | WO 2007/062112 A2 | 5/2007 |
| WO | WO 2010/049465 A1 | 5/2010 |
| WO | WO 2013/062679 A1 | 5/2013 |
| WO | WO 2017/090193 A1 | 6/2017 |

OTHER PUBLICATIONS

Lai et al., "Surfactants and Detergents," Advances in Fine Petrochemicals, vol. 11. No. 3, 1997, 53 pages total, with an English translation.

"Synthesis and Application of Aliphatic Glycidyl Ethers," China Academic Journal Electronic Publishing House, 1995, pp. 15-21.

English translation of the Chinese Search Report for Chinese Application No. 202080030437.3, dated May 31, 2022.

Extended European Search Report for European Application No. 20812820.7, dated Jul. 1, 2022.

Extended European Search Report for European Application No. 20813026.0, dated Jul. 1, 2022.

Extended European Search Report for European Application No. 20813622.6, dated Jul. 1, 2022.

Extended European Search Report for European Application No. 20814785.0, dated Jun. 24, 2022.

International Search Report for International Application No. PCT/JP2020/021174, dated Aug. 11, 2020.

International Search Report for International Application No. PCT/JP2020/021194, dated Aug. 18, 2020.

International Search Report for International Application No. PCT/JP2020/021208, dated Aug. 25, 2020.

International Search Report for International Application No. PCT/JP2020/021211, dated Aug. 18, 2020.

International Search Report for International Application No. PCT/JP2020/021213, dated Jul. 21, 2020.

U.S. Appl. No. 17/604,816, filed Oct. 19, 2021.

U.S. Appl. No. 17/605,729, filed Oct. 22, 2021.

U.S. Appl. No. 17/605,705, filed Oct. 22, 2021.

U.S. Appl. No. 17/605,921, filed Oct. 22, 2021.

International Preliminary Report on Patentability and English translation of the Written Opinion of the International Searching Authority for International Application No. PCT/JP2020/021174, dated Dec. 9, 2021.

International Preliminary Report on Patentability and English translation of the Written Opinion of the International Searching Authority for International Application No. PCT/JP2020/021194, dated Dec. 9, 2021.

International Preliminary Report on Patentability and English translation of the Written Opinion of the International Searching Authority for International Application No. PCT/JP2020/021208, dated Dec. 9, 2021.

International Preliminary Report on Patentability and English translation of the Written Opinion of the International Searching Authority for International Application No. PCT/JP2020/021211, dated Dec. 9, 2021.

International Preliminary Report on Patentability and English translation of the Written Opinion of the International Searching Authority for International Application No. PCT/JP2020/021213, dated Dec. 9, 2021.

* cited by examiner

SURFACTANT AND SURFACTANT COMPOSITION

TECHNICAL FIELD

The present invention relates to a surfactant, and a surfactant composition containing the surfactant.

BACKGROUND ART

Ether alcohols obtained by reaction of an epoxy alkane with a polyhydric alcohol are useful as raw materials for an emulsifier, a surfactant, a dispersant, and the like.

For example, Patent Document 1 discloses an ether alcohol obtained by reaction of an epoxy alkane having 8 to 20 carbon atoms with a mono- or polyfunctional alcohol having 1 to 10 carbon atoms and 1 to 4 alcoholic hydroxyl groups.

In addition, Patent Document 2 discloses a glyceryl etherified polyhydric alcohol represented by the following general Formula (1):

G[(AO)xB]y    (1)

wherein G represents a polyhydric alcohol residue, at least one of B represents a branched alkyloxyglyceryl group, and the remainder represents a hydrogen atom.

PRIOR ART DOCUMENTS

Patent Document

Patent Document 1: JP-A-55-105632
Patent Document 2: JP-A-5-984

SUMMARY OF THE INVENTION

Problems To be Solved by the Invention

The present invention provides a surfactant excellent in emulsifiability to oils, wettability to substances, permeability to textile products, and detergency, and a surfactant composition containing the surfactant.

Means for Solving the Problems

As a result of intensive studies, the present inventor has found that the above problems can be solved by the following surfactant.

The present invention relates to a surfactant comprising at least one kind of a compound represented by a Chemical Formula (1):

[Chemical Formula (1)]

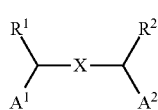

wherein $R^1$ is a hydrogen atom or an aliphatic hydrocarbon group having 1 or more and 33 or less carbon atoms, $R^2$ is an aliphatic hydrocarbon group having 1 or more and 33 or less carbon atoms, a total number of carbon atoms of $R^1$ and $R^2$ is 1 or more and 34 or less, X is a single bond or an aliphatic hydrocarbon group having 1 or more and 5 or less carbon atoms, and one of $A^1$ and $A^2$ is —OH and the other is —O—$CH_2$—CH(OH)—$CH_2$OH or —O—CH(—$CH_2$—OH)$_2$.

Effect of the Invention

The compound represented by the Chemical Formula (1) (hereinafter, also referred to as ether alcohol) is characterized by having a glyceryl ether group and a hydroxyl group, and the surfactant containing at least one kind of the ether alcohol is excellent in emulsifiability to oils, wettability to substances, permeability to textile products, and detergency.

MODE FOR CARRYING OUT THE INVENTION

Hereinafter, a detailed described is made of the present invention.

Surfactant

The surfactant of the present invention contains at least one kind of a compound represented by the following Chemical Formula (1). In addition, the surfactant of the present invention may be composed of a compound represented by the following Chemical Formula (1). In addition, the surfactant of the present invention may be composed of one or more kinds of a compound represented by the following Chemical Formula (1).

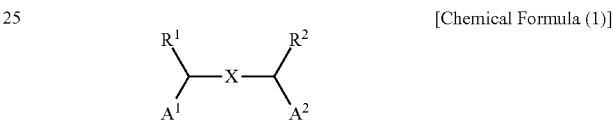

[Chemical Formula (1)]

(In Chemical Formula (1), $R^1$ is a hydrogen atom or an aliphatic hydrocarbon group having 1 or more and 33 or less carbon atoms, $R^2$ is an aliphatic hydrocarbon group having 1 or more and 33 or less carbon atoms, a total number of carbon atoms of $R^1$ and $R^2$ is 1 or more and 34 or less, X is a single bond or an aliphatic hydrocarbon group having 1 or more and 5 or less carbon atoms, and one of $A^1$ and $A^2$ is —OH and the other is —O—$CH_2$—CH(OH)—$CH_2$OH or —O—CH(—$CH_2$—OH)$_2$.)

$R^1$ is a hydrogen atom or an aliphatic hydrocarbon group having 1 or more and 33 or less carbon atoms, and is preferably an aliphatic hydrocarbon group having 1 or more and 33 or less carbon atoms from the viewpoint of improving emulsifiability to oils, wettability to a substance, permeability to a textile product and detergency. $R^2$ is an aliphatic hydrocarbon group having 1 or more and 33 or less carbon atoms. Each of the aliphatic hydrocarbon groups of $R^1$ and $R^2$ is preferably a linear alkyl group or a branched alkyl group (also referred to as a branched chain alkyl group), more preferably a linear alkyl group. Each of the aliphatic hydrocarbon groups of $R^1$ and $R^2$ may have a substituent such as a halogen group, a hydroxy group, a ketone group, a carboxyl group, an aryl group, or an alkoxy group as long as the effect of the present invention is not impaired. $R^1$ and $R^2$ may be the same aliphatic hydrocarbon groups as each other or different aliphatic hydrocarbon groups from each other. In addition, the total number of substituents of $R^1$ and $R^2$ is preferably 5 or less, more preferably 3 or less, further preferably 1 or less, still more preferably 0 (that is, having no substituent) from the viewpoint of improving emulsifiability to oils, wettability to substances, permeability to textile products, and detergency.

The total number of carbon atoms of $R^1$ and $R^2$ is 1 or more and 34 or less, or from the viewpoint of improving emulsifiability to oils, wettability to substances, permeability to textile products, and detergency, preferably 4 or more, more preferably 8 or more, further preferably 12 or more, still more preferably 16 or more, and preferably 24 or less, more preferably 22 or less, further preferably 20 or less, still more preferably 18 or less.

X is a single bond or an aliphatic hydrocarbon group having 1 or more and 5 or less carbon atoms, or from the viewpoint of improving emulsifiability to oils, wettability to substances, permeability to textile products, and detergency, preferably a single bond or an aliphatic hydrocarbon group having 1 or more and 3 or less carbon atoms, more preferably a single bond or an aliphatic hydrocarbon group having 1 or more and 2 or less carbon atoms, further preferably a single bond or an aliphatic hydrocarbon group having 1 carbon atom, still more preferably a single bond.

The total number of carbon atoms of $R^1$, $R^2$ and X is 1 or more and 39 or less, or from the viewpoint of improving emulsifiability to oils, wettability to substances, permeability to textile products, and detergency, preferably 4 or more, more preferably 8 or more, further preferably 12 or more, still more preferably 16 or more, and preferably 31 or less, more preferably 28 or less, further preferably 26 or less, still more preferably 25 or less, still more preferably 24 or less, still more preferably 22 or less, still more preferably 20 or less, still more preferably 18 or less.

When X is the aliphatic hydrocarbon group, X is preferably a linear alkyl group or branched alkyl group, more preferably a linear alkyl group from the viewpoint of improving emulsifiability to oils, wettability to substances, permeability to textile products, and detergency.

From the viewpoint of improving emulsifiability to oils, wettability to substances, permeability to textile products, and detergency, X is preferably

*—$(CH_2)_n$—* (n is 0 or more and 5 or less, and * represents a binding site), wherein n is preferably 0 or more, preferably 3 or less, more preferably 2 or less, further preferably 1 or less, still more preferably 0, that is, a single bond.

From the viewpoint of improving emulsifiability to oils, wettability to substances, permeability to textile products, and detergency, the surfactant preferably contains two or more kinds of the compound, between which the total numbers of carbon atoms of $R^1$ and $R^2$ are the same, but the numbers of carbon atoms of $R^1$ and the numbers of carbon atoms of $R^2$ are each different.

From the viewpoint of improving emulsifiability to oils, wettability to substances, permeability to textile products, and detergency, the surfactant preferably contains two or more kinds of the compound, between which the total numbers of carbon atoms of $R^1$, $R^2$ and X are the same, but the numbers of carbon atoms of $R^1$ and the numbers of carbon atoms of $R^2$ are each different.

From the viewpoint of improving emulsifiability to oils, wettability to substances, permeability to textile products, and detergency, the surfactant preferably contains two or more kinds of the compound in which X is a single bond or an aliphatic hydrocarbon group having 1 or more and 3 or less carbon atoms, and between which the total numbers of carbon atoms of $R^1$ and $R^2$ are the same, but the numbers of carbon atoms of $R^1$ and the numbers of carbon atoms of $R^2$ are each different.

From the viewpoint of improving emulsifiability to oils, wettability to substances, permeability to textile products, and detergency, the surfactant preferably contains two or more kinds of the compound in which X is a single bond or an aliphatic hydrocarbon group having 1 or more and 3 or less carbon atoms, and between which the total numbers of carbon atoms of $R^1$, $R^2$ and X are the same, but the numbers of carbon atoms of $R^1$ and the numbers of carbon atoms of $R^2$ are each different.

From the viewpoint of improving emulsifiability to oils, wettability to substances, permeability to textile products, and detergency, the surfactant preferably contains two or more kinds of the compound in which X is a single bond or an aliphatic hydrocarbon group having 1 or more and 2 or less carbon atoms, and between which the total numbers of carbon atoms of $R^1$ and $R^2$ are the same, but the numbers of carbon atoms of $R^1$ and the numbers of carbon atoms of $R^2$ are each different.

From the viewpoint of improving emulsifiability to oils, wettability to substances, permeability to textile products, and detergency, the surfactant preferably contains two or more kinds of the compound in which X is a single bond or an aliphatic hydrocarbon group having 1 or more and 2 or less carbon atoms, and between which the total numbers of carbon atoms of $R^1$, $R^2$ and X are the same, but the numbers of carbon atoms of $R^1$ and the numbers of carbon atoms of $R^2$ are each different.

From the viewpoint of improving emulsifiability to oils, wettability to substances, permeability to textile products, and detergency, the surfactant preferably contains two or more kinds of the compound in which X is a single bond or an aliphatic hydrocarbon group having 1 carbon atom, and between which the total numbers of carbon atoms of $R^1$ and $R^2$ are the same, but the numbers of carbon atoms of $R^1$ and the numbers of carbon atoms of $R^2$ are each different.

From the viewpoint of improving emulsifiability to oils, wettability to substances, permeability to textile products, and detergency, the surfactant preferably contains two or more kinds of the compound in which X is a single bond or an aliphatic hydrocarbon group having 1 carbon atom, and between which the total numbers of carbon atoms of $R^1$, $R^2$ and X are the same, but the numbers of carbon atoms of $R^1$ and the numbers of carbon atoms of $R^2$ are each different.

From the viewpoint of improving emulsifiability to oils, wettability to substances, permeability to textile products, and detergency, the surfactant preferably contains two or more kinds of the compound in which X is a single bond, and between which the total numbers of carbon atoms of $R^1$ and $R^2$ are the same, but the numbers of carbon atoms of $R^1$ and the numbers of carbon atoms of $R^2$ are each different.

When the surfactant contains two or more kinds of the compound in which X is a single bond and between which the total numbers of carbon atoms of $R^1$ and $R^2$ are different, the total content of two or more kinds of the compound selected from a compound in which the total number of carbon atoms of $R^1$ and $R^2$ is 12, a compound in which the total number of carbon atoms of $R^1$ and $R^2$ is 14, and a compound in which the total number of carbon atoms of $R^1$ and $R^2$ is 16 is preferably 75 mass % or more, more preferably 85 mass % or more, further preferably 95 mass % or more, still more preferably 100 mass % from the viewpoint of improving emulsifiability to oils, wettability to substances, permeability to textile products, and detergency.

When the surfactant contains two or more kinds of the compound in which X is a single bond and between which the total numbers of carbon atoms of $R^1$ and $R^2$ are different, the total content of two or more kinds of the compound selected from a compound in which the total number of carbon atoms of $R^1$ and $R^2$ is 14, and a compound in which the total number of carbon atoms of $R^1$ and $R^2$ is 16 is preferably 75 mass % or more, more preferably 85 mass % or more, further preferably 95 mass % or more, still more preferably 99 mass % or more, still more preferably 100 mass % from the viewpoint of improving emulsifiability to oils, wettability to substances, permeability to textile products, and detergency.

When the surfactant contains two or more kinds of the compound represented by the Chemical Formula (1) between which the total numbers of carbon atoms of $R^1$ and $R^2$ are the same, but the numbers of carbon atoms of $R^1$ and the numbers of carbon atoms of $R^2$ are each different, the content ratio of the compound in which the number of carbon atoms of $R^1$ is 5 or more and the number of carbon atoms of $R^2$ is 5 or more is preferably 10 mass % or more, more preferably 20 mass % or more, further preferably 30 mass % or more, and preferably 90 mass % or less, more preferably 80 mass % or less, further preferably 70 mass % or less from the viewpoint of improving emulsifiability to oils, wettability to substances, permeability to textile products, and detergency.

The method for producing the compound represented by the Chemical Formula (1) is not particularly limited. For example, the compound can be produced by oxidizing the double bond in an internal or terminal olefin with a peroxide such as hydrogen peroxide, performic acid, or peracetic acid to synthesize an internal or terminal epoxide, and reacting the obtained internal or terminal epoxide with glycerin. In the case of a mixture in which the total numbers of carbon atoms of internal or terminal olefins are constant but the double bonds are present at different positions, the compound represented by the Chemical Formula (1) obtained by the above producing method is a mixture of a plurality of compounds in which X is a single bond and between which the total numbers of carbon atoms of $R^1$ and $R^2$ are the same, but the numbers of carbon atoms of $R^1$ and the numbers of carbon atoms of $R^2$ are each different. The compound represented by the Chemical Formula (1) obtained by the above producing method is usually a mixture of a compound 1 in which one of $A^1$ and $A^2$ is —OH and the other is —O—CH$_2$—CH(OH)—CH$_2$OH (hereinafter, also referred to as ether alcohol 1) and a compound 2 in which one of $A^1$ and $A^2$ is —OH and the other is —O—CH(—CH$_2$—OH)$_2$ (hereinafter, also referred to as ether alcohol 2).

The internal olefin used for the production of the compound represented by the Chemical Formula (1) may contain a terminal olefin. In this case, the content of terminal olefin contained in olefin is, for example, 0.1 mass % or more, 0.2 mass % or more, and 5 mass % or less, 3 mass % or less, 2 mass % or less, 1 mass % or less, 0.5 mass % or less.

When the surfactant contains the ether alcohol 1 and the ether alcohol 2, the content of the ether alcohol 1 is preferably 1 mass % or more, more preferably 30 mass % or more, further preferably 40 mass % or more, still more preferably 50 mass % or more, and preferably 99 mass % or less, more preferably 90 mass % or less, further preferably 80 mass % or less with respect to the total amount of the ether alcohol 1 and the ether alcohol 2, from the viewpoint of improving emulsifiability to oils, wettability to substances, permeability to textile products, and detergency. From the same viewpoint, the content is preferably 1 to 99 mass %, more preferably 30 to 99 mass %, further preferably 40 to 90 mass %, still more preferably 50 to 80 mass %.

The surfactant can be obtained as one kind of the compound represented by the Chemical Formula (1), a mixture of two or more kinds of the compound represented by the Chemical Formula (1), or a mixture of the above compound and a trace component other than olefin contained in the raw material olefin and a derivative thereof.

The surfactant may be an emulsifier, a wetting agent, a penetrant, an agent for oil recovery, or a detergent. That is, the surfactant of the present invention may be an emulsifier, a wetting agent, a penetrant, an agent for oil recovery, or a detergent containing one or more kinds of the compound represented by the Chemical Formula (1). In addition, the surfactant of the present invention may be an emulsifier, a wetting agent, a penetrant, an agent for oil recovery, or a detergent composed of the compound represented by the Chemical Formula (1). In addition, the surfactant of the present invention may be an emulsifier, a wetting agent, a penetrant, an agent for oil recovery, or a detergent composed of one or more kinds of the compound represented by the Chemical Formula (1). The agent for oil recovery is preferably an agent for crude oil recovery, more preferably an agent for EOR (Enhanced Oil Recovery, the same hereinafter), further preferably an agent for chemical EOR.

Surfactant Composition

The surfactant composition of the present invention contains at least the surfactant.

The content of the surfactant in the surfactant composition is not particularly limited, but is preferably 0.01 mass % or more, more preferably 0.05 mass % or more, further preferably 0.1 mass % or more, and preferably 15 mass % or less, more preferably 10 mass % or less, further preferably 5 mass % or less from the viewpoint of improving the emulsifiability to oils, wettability to substances, permeability to textile products, and detergency.

The surfactant composition of the present invention may optionally contain a component or the like for use in a detergent such as a surfactant other than the ether alcohol, a solvent, a perfume, a dye, a preservative, a moisturizing agent, an antibacterial agent, an anti-dandruff agent, a pearling agent, a vitamin agent, a thickener, a pH adjuster, a bleaching agent, a chelating agent, a water-soluble salt, or an oil agent as long as the effect of the present invention is not impaired.

Examples of the surfactant other than the ether alcohol include an anionic surfactant, a nonionic surfactant other than the ether alcohol, an amphoteric surfactant, and a cationic surfactant. These may be used alone or in combination of two or more kinds thereof.

Examples of the anionic surfactant include sulfuric acid ester salts such as alkyl sulfate, alkenyl sulfate, polyoxyalkylene alkyl ether sulfate, polyoxyalkylene alkenyl ether sulfate, and polyoxyalkylene alkyl phenyl ether sulfate; sulfonates such as sulfosuccinic acid alkyl ester salt, polyoxyalkylene sulfosuccinic acid alkyl ester salt, alkanesulfonate, hydroxyalkanesulfonate, alkenesulfonate, acyl isethionate, and acyl methyl taurate; higher fatty acid salts having 8 to 24 carbon atoms; phosphate ester salts such as alkyl phosphate and polyoxyalkylene alkyl ether phosphate; and amino acid salts such as acyl glutamate, alanine derivatives, glycine derivatives, and arginine derivatives. Examples of these salts include alkali metal salts such as sodium salt and potassium salt; alkaline earth metal salts such as calcium salt and magnesium salt; and ammonium salts. These may be used alone or in combination of two or more kinds thereof.

Examples of the nonionic surfactant other than the ether alcohol include polyethylene glycol kind surfactants such as polyoxyethylene sorbitan fatty acid ester, polyoxyethylene sorbit fatty acid ester, polyoxyethylene glycerin fatty acid ester, polyoxyethylene fatty acid ester, polyoxyethylene alkylphenyl ether, and polyoxyalkylene (cured) castor oil; polyhydric alcohol kinds such as sucrose fatty acid ester, polyglycerol alkyl ether, polyglycerol fatty acid ester, alkyl glycoside, and acylated alkyl glucamide; and fatty acid alkanolamides. Specific examples thereof include fatty acid monoalkanolamides such as coconut oil fatty acid monoethanolamide and coconut oil fatty acid N-methyl monoethanolamide. These may be used alone or in combination of two or more kinds thereof.

Examples of the amphoteric surfactant include betaine-based surfactants such as imidazoline-based betaine, alkyldimethylaminoacetic acid betaine, fatty acid amidopropyl betaine, and sulfobetaine; amine oxide kind surfactants such as alkyldimethylamine oxide. Specific examples thereof include coconut oil fatty acid amidopropyl dimethylcarbobetaine, lauramidopropyl dimethylcarbobetaine, laurylcarboxymethyl hydroxyimidazolium betaine, lauryldimethylaminoacetic acid betaine, and laurylhydroxysulfobetaine. These may be used alone or in combination of two or more kinds thereof.

Examples of the cationic surfactant include quaternary ammonium salts having a hydrocarbon group having 12 or more and 28 or less carbon atoms which may be divided by an amide group, an ester group, or an ether group; pyridinium salts; and salts of mineral acid or organic acid of tertiary amine. Specific examples include mono-long chain alkyl trimethyl ammonium salts such as octyl trimethyl ammonium salt, decyl trimethyl ammonium salt, lauryl trimethyl ammonium salt, myristyl trimethyl ammonium salt, cetyl trimethyl ammonium salt, stearyl trimethyl ammonium salt, behenyl trimethyl ammonium salt, and octadecyloxypropyl trimethyl ammonium salt; di-long chain alkyldimethylammonium salts such as dioctyldimethylammonium salt, didecyldimethylammonium salt, dilauryldimethylammonium salt, dimyristyldimethylammonium salt, dicetyldimethylammonium salt, distearyldimethylammonium salt, and diisotetradecyldimethylammonium salt; and hydrochlorides, citrates, or lactates of mono-long chain alkyldimethylamine such as stearyldimethylamine, behenyldimethylamine, octadecyloxypropyldimethylamine, or dimethylaminopropylstearic acid amide. The ammonium salts may be halogen salts such as ammonium chloride, bromide, or iodide. These may be used alone or in combination of two or more kinds thereof.

The surfactant composition of the present invention can contain a solvent for the purpose of, for example, improving low-temperature stability and washing performance. Examples of the solvent include alcohols, glycol ethers, and alkylene glycol alkyl ethers. Examples of the alcohol include monohydric alcohols such as ethanol, isopropyl alcohol, and butanol, polyhydric alcohols such as ethylene glycol, propylene glycol, butylene glycol, hexylene glycol (2-methyl-2, 4-pentanediol), 1,5-pentanediol, 1,6-hexanediol, and glycerin, and aromatic alcohols such as benzyl alcohol. Examples of the alkylene glycol ether include diethylene glycol, triethylene glycol, tetraethylene glycol, dipropylene glycol, and tripropylene glycol. Examples of the alkylene glycol alkyl ether include diethylene glycol monomethyl ether, triethylene glycol monomethyl ether, diethylene glycol monoethyl ether, dipropylene glycol monomethyl ether, dipropylene glycol monoethyl ether, tripropylene glycol monomethyl ether, diethylene glycol monobutyl ether, 1-methoxy-2 propanol and 1-ethoxy-2-propanol, 2-phenoxyethanol, diethylene glycol monophenyl ether, and triethylene glycol monophenyl ether. These may be used alone or in combination of two or more kinds thereof.

In the present invention, the content of the solvent in the surfactant composition is preferably 30 mass % or less, more preferably 20 mass % or less, further preferably 10 mass % or less, still more preferably 5 mass % or less, still more preferably 1 mass % or less, still more preferably 0 mass %, that is, it is preferable that the surfactant composition does not contain a solvent, from the viewpoint of sustainability, environmental load, safety, and the like.

The surfactant composition may be an emulsifier composition, a wetting agent composition, a penetrant composition, a composition for oil recovery, or a detergent composition. That is, the surfactant composition of the present invention may be an emulsifier composition, a wetting agent composition, a penetrant composition, a composition for oil recovery, or a detergent composition containing one or more kinds of the compound represented by the Chemical Formula (1). The composition for oil recovery is preferably a composition for crude oil recovery, more preferably a composition for EOR (Enhanced Oil Recovery, the same hereinafter), further preferably a composition for chemical EOR.

The surfactant and the surfactant composition of the present invention are used as, for example, a detergent such as a liquid detergent for clothing, a detergent for dishware, a detergent for hair, a detergent for body, a detergent for precision parts, and a detergent for hard surfaces. The surfactant and the surfactant composition of the present invention can be used for the respective cleaning applications when added to water and dissolved.

The present invention and preferred embodiments of the present invention are described below.

<1>

A surfactant comprising at least one kind of a compound represented by a Chemical Formula (1):

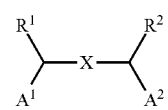

[Chemical Formula (1)]

wherein $R^1$ is a hydrogen atom or an aliphatic hydrocarbon group having 1 or more and 33 or less carbon atoms, $R^2$ is an aliphatic hydrocarbon group having 1 or more and 33 or less carbon atoms, a total number of carbon atoms of $R^1$ and $R^2$ is 1 or more and 34 or less, X is a single bond or an aliphatic hydrocarbon group having 1 or more and 5 or less carbon atoms, and one of $A^1$ and $A^2$ is —OH and the other is —O—$CH_2$—CH(OH)—$CH_2$OH or —O—CH(—$CH_2$—OH)$_2$.

<2>

A surfactant comprising at least one kind of a compound represented by a Chemical Formula (1):

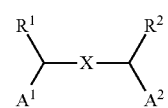

[Chemical Formula (1)]

wherein $R^1$ is a hydrogen atom or an aliphatic hydrocarbon group having 1 or more and 33 or less carbon atoms, $R^2$ is an aliphatic hydrocarbon group having 1 or more and 33 or less carbon atoms, X is a single bond or an aliphatic hydrocarbon group having 1 or more and 5 or less carbon atoms, a total number of carbon atoms of $R^1$, $R^2$ and X is 1 or more and 39 or less, and one of $A^1$ and $A^2$ is —OH and the other is —O—$CH_2$—CH(OH)—$CH_2$OH or —O—CH(—$CH_2$—OH)$_2$.

<3>

The surfactant according to <1> or <2>, wherein $R^1$ is an aliphatic hydrocarbon group having 1 or more and 33 or less carbon atoms.

<4>

The surfactant according to any one of <1> to <3>, wherein each of the aliphatic hydrocarbon groups of $R^1$ and $R^2$ is preferably a linear alkyl group or a branched alkyl group, more preferably a linear alkyl group.

<5>

The surfactant according to any one of <1> to <4>, wherein a total number of substituents of $R^1$ and $R^2$ is preferably 5 or less, more preferably 3 or less, further preferably 1 or less, still more preferably 0.

<6>

The surfactant according to any one of <1> to <5>, wherein a total number of carbon atoms of $R^1$ and $R^2$ is preferably 4 or more, more preferably 8 or more, further preferably 12 or more, still more preferably 16 or more, and preferably 24 or less, more preferably 22 or less, further preferably 20 or less, still more preferably 18 or less.

<7>

The surfactant according to any one of <1> to <6>, wherein X is preferably a single bond or an aliphatic hydrocarbon group having 1 or more and 3 or less carbon atoms, more preferably a single bond or an aliphatic hydrocarbon group having 1 or more and 2 or less carbon atoms, further preferably a single bond or an aliphatic hydrocarbon group having 1 carbon atom, still more preferably a single bond.

<8>

The surfactant according to any one of <1> to <5>, wherein preferably a total number of carbon atoms of $R^1$ and $R^2$ is 4 or more and 24 or less, and X is a single bond or an aliphatic hydrocarbon group having 1 or more and 3 or less carbon atoms, more preferably a total number of carbon atoms of $R^1$ and $R^2$ is 8 or more and 22 or less, and X is a single bond or an aliphatic hydrocarbon group having 1 or more and 2 or less carbon atoms, further preferably a total number of carbon atoms of $R^1$ and $R^2$ is 12 or more and 20 or less, and X is a single bond or an aliphatic hydrocarbon group having 1 carbon atom, still more preferably a total number of carbon atoms of $R^1$ and $R^2$ is 16 or more and 18 or less, and X is a single bond.

<9>

The surfactant according to any one of <1> to <8>, wherein a total number of carbon atoms of $R^1$, $R^2$ and X is preferably 4 or more, more preferably 8 or more, further preferably 12 or more, still more preferably 16 or more, and preferably 31 or less, more preferably 28 or less, further preferably 26 or less, still more preferably 25 or less, still more preferably 24 or less, still more preferably 22 or less, still more preferably 20 or less, still more preferably 18 or less.

<10>

The surfactant according to any one of <1> to <9>, wherein when X is the aliphatic hydrocarbon group, X is preferably a linear alkyl group or branched alkyl group, more preferably a linear alkyl group.

<11>

The surfactant according to any one of <1> to <9>, wherein X is

*—$(CH_2)_n$—* (n is 0 or more and 5 or less, and * represents a binding site), wherein n is preferably 0 or more, preferably 3 or less, more preferably 2 or less, further preferably 1 or less, still more preferably 0, that is, a single bond.

<12>

The surfactant according to any one of <1> to <11>, comprising two or more kinds of the compound in which X is a single bond or an aliphatic hydrocarbon group having 1 or more and 3 or less carbon atoms, and between which the total numbers of carbon atoms of $R^1$ and $R^2$ are the same, but the numbers of carbon atoms of $R^1$ and the numbers of carbon atoms of $R^2$ are each different.

<13>

The surfactant according to any one of <1> to <11>, comprising two or more kinds of the compound in which X is a single bond or an aliphatic hydrocarbon group having 1 or more and 3 or less carbon atoms, and between which the total numbers of carbon atoms of $R^1$, $R^2$ and X are the same, but the numbers of carbon atoms of $R^1$ and the numbers of carbon atoms of $R^2$ are each different.

<14>

The surfactant according to any one of <1> to <11>, comprising two or more kinds of the compound in which X is a single bond or an aliphatic hydrocarbon group having 1 or more and 2 or less carbon atoms, and between which the total numbers of carbon atoms of $R^1$ and $R^2$ are the same, but the numbers of carbon atoms of $R^1$ and the numbers of carbon atoms of $R^2$ are each different.

<15>

The surfactant according to any one of <1> to <11>, comprising two or more kinds of the compound in which X is a single bond or an aliphatic hydrocarbon group having 1 or more and 2 or less carbon atoms, and between which the total numbers of carbon atoms of $R^1$, $R^2$ and X are the same, but the numbers of carbon atoms of $R^1$ and the numbers of carbon atoms of $R^2$ are each different.

<16>

The surfactant according to any one of <1> to <11>, comprising two or more kinds of the compound in which X is a single bond or an aliphatic hydrocarbon group having 1 carbon atom, and between which the total numbers of carbon atoms of $R^1$ and $R^2$ are the same, but the numbers of carbon atoms of $R^1$ and the numbers of carbon atoms of $R^2$ are each different.

<17>

The surfactant according to any one of <1> to <11>, comprising two or more kinds of the compound in which X is a single bond or an aliphatic hydrocarbon group having 1 carbon atom, and between which the total numbers of carbon atoms of $R^1$, $R^2$ and X are the same, but the numbers of carbon atoms of $R^1$ and the numbers of carbon atoms of $R^2$ are each different.

<18>

The surfactant according to any one of <1> to <11>, comprising two or more kinds of the compound in which X is a single bond, and between which the total numbers of carbon atoms of $R^1$ and $R^2$ are the same, but the numbers of carbon atoms of $R^1$ and the numbers of carbon atoms of $R^2$ are each different.

<19>

The surfactant according to any one of <1> to <9>, wherein when the surfactant contains two or more kinds of the compound in which X is a single bond and between which the total numbers of carbon atoms of $R^1$ and $R^2$ are different, the total content of two or more kinds of the compound selected from a compound in which the total number of carbon atoms of $R^1$ and $R^2$ is 12, a compound in which the total number of carbon atoms of $R^1$ and $R^2$ is 14, and a compound in which the total number of carbon atoms of $R^1$ and $R^2$ is 16 is 75 mass % or more.

<20>
The surfactant according to any one of <1> to <9>, wherein when the surfactant contains two or more kinds of the compound in which X is a single bond and between which the total numbers of carbon atoms of $R^1$ and $R^2$ are different, the total content of two or more kinds of the compound selected from a compound in which the total number of carbon atoms of $R^1$ and $R^2$ is 12, a compound in which the total number of carbon atoms of $R^1$ and $R^2$ is 14, and a compound in which the total number of carbon atoms of $R^1$ and $R^2$ is 16 is 85 mass % or more.

<21>
The surfactant according to any one of <1> to <9>, wherein when the surfactant contains two or more kinds of the compound in which X is a single bond and between which the total numbers of carbon atoms of $R^1$ and $R^2$ are different, the total content of two or more kinds of the compound selected from a compound in which the total number of carbon atoms of $R^1$ and $R^2$ is 12, a compound in which the total number of carbon atoms of $R^1$ and $R^2$ is 14, and a compound in which the total number of carbon atoms of $R^1$ and $R^2$ is 16 is 95 mass % or more.

<22>
The surfactant according to any one of <1> to <9>, wherein when the surfactant contains two or more kinds of the compound in which X is a single bond and between which the total numbers of carbon atoms of $R^1$ and $R^2$ are different, the total content of two or more kinds of the compound selected from a compound in which the total number of carbon atoms of $R^1$ and $R^2$ is 12, a compound in which the total number of carbon atoms of $R^1$ and $R^2$ is 14, and a compound in which the total number of carbon atoms of $R^1$ and $R^2$ is 16 is 100 mass %.

<23>
The surfactant according to any one of <1> to <9>, wherein when the surfactant contains two or more kinds of the compound in which X is a single bond and between which the total numbers of carbon atoms of $R^1$ and $R^2$ are different, the total content of two or more kinds of the compound selected from a compound in which the total number of carbon atoms of $R^1$ and $R^2$ is 14, and a compound in which the total number of carbon atoms of $R^1$ and $R^2$ is 16 is 75 mass % or more.

<24>
The surfactant according to any one of <1> to <9>, wherein when the surfactant contains two or more kinds of the compound in which X is a single bond and between which the total numbers of carbon atoms of $R^1$ and $R^2$ are different, the total content of two or more kinds of the compound selected from a compound in which the total number of carbon atoms of $R^1$ and $R^2$ is 14, and a compound in which the total number of carbon atoms of $R^1$ and $R^2$ is 16 is 85 mass % or more.

<25>
The surfactant according to any one of <1> to <9>, wherein when the surfactant contains two or more kinds of the compound in which X is a single bond and between which the total numbers of carbon atoms of $R^1$ and $R^2$ are different, the total content of two or more kinds of the compound selected from a compound in which the total number of carbon atoms of $R^1$ and $R^2$ is 14, and a compound in which the total number of carbon atoms of $R^1$ and $R^2$ is 16 is 95 mass % or more.

<26>
The surfactant according to any one of <1> to <9>, wherein when the surfactant contains two or more kinds of the compound in which X is a single bond and between which the total numbers of carbon atoms of $R^1$ and $R^2$ are different, the total content of two or more kinds of the compound selected from a compound in which the total number of carbon atoms of $R^1$ and $R^2$ is 14, and a compound in which the total number of carbon atoms of $R^1$ and $R^2$ is 16 is 99 mass % or more, preferably 100 mass %.

<27>
The surfactant according to any one of <1> to <18>, wherein when the surfactant contains two or more kinds of the compound represented by the Chemical Formula (1) between which the total numbers of carbon atoms of $R^1$ and $R^2$ are the same, but the numbers of carbon atoms of $R^1$ and the numbers of carbon atoms of $R^2$ are each different, the content ratio of the compound in which the number of carbon atoms of $R^1$ is 5 or more and the number of carbon atoms of $R^2$ is 5 or more is 10 mass % or more and 90 mass % or less.

<28>
The surfactant according to any one of <1> to <18>, wherein when the surfactant contains two or more kinds of the compound represented by the Chemical Formula (1) between which the total numbers of carbon atoms of $R^1$ and $R^2$ are the same, but the numbers of carbon atoms of $R^1$ and the numbers of carbon atoms of $R^2$ are each different, the content ratio of the compound in which the number of carbon atoms of $R^1$ is 5 or more and the number of carbon atoms of $R^2$ is 5 or more is 20 mass % or more and 80 mass % or less.

<29>
The surfactant according to any one of <1> to <18>, wherein when the surfactant contains two or more kinds of the compound represented by the Chemical Formula (1) between which the total numbers of carbon atoms of $R^1$ and $R^2$ are the same, but the numbers of carbon atoms of $R^1$ and the numbers of carbon atoms of $R^2$ are each different, the content ratio of the compound in which the number of carbon atoms of $R^1$ is 5 or more and the number of carbon atoms of $R^2$ is 5 or more is 30 mass % or more and 70 mass % or less.

<30>
The surfactant according to any one of <1> to <29>, comprising a compound 1 in which in the Chemical Formula (1), one of $A^1$ and $A^2$ is —OH and the other is —O—$CH_2$—CH(OH)—$CH_2$OH, and a compound 2 in which in the Chemical Formula (1), one of $A^1$ and $A^2$ is —OH and the other is —O—CH(—$CH_2$—OH)$_2$.

<31>
The surfactant according to <30>, wherein a content of the compound 1 is preferably 1 mass % or more, more preferably 30 mass % or more, further preferably 40 mass % or more, still more preferably 50 mass % or more, and preferably 99 mass % or less, more preferably 90 mass % or less, further preferably 80 mass % or less with respect to a total amount of the compound 1 and the compound 2.

<32>
The surfactant according to <30>, wherein a content of the compound 1 is 1 to 99 mass % with respect to a total amount of the compound 1 and the compound 2.

<33>
The surfactant according to <30>, wherein a content of the compound 1 is 30 to 99 mass % with respect to a total amount of the compound 1 and the compound 2.

<34>
The surfactant according to <30>, wherein a content of the compound 1 is 40 to 90 mass % with respect to a total amount of the compound 1 and the compound 2.
<35>
The surfactant according to <30>, wherein a content of the compound 1 is 50 to 80 mass % with respect to a total amount of the compound 1 and the compound 2.
<36>
The surfactant according to any one of <1> to <35>, being an emulsifier, a wetting agent, a penetrant, an agent for oil recovery, or a detergent.
<37>
The surfactant according to any one of <1> to <35>, being an emulsifier, a wetting agent, a penetrant, an agent for oil recovery, or a detergent containing one or more kinds of the compound represented by the Chemical Formula (1).
<38>
The surfactant according to any one of <1> to <35>, being an emulsifier, a wetting agent, a penetrant, an agent for oil recovery, or a detergent composed of the compound represented by the Chemical Formula (1).
<39>
The surfactant according to any one of <1> to <35>, being an emulsifier, a wetting agent, a penetrant, an agent for oil recovery, or a detergent composed of one or more kinds of the compound represented by the Chemical Formula (1).
<40>
The surfactant according to any one of <36> to <39>, wherein the agent for oil recovery is preferably an agent for crude oil recovery, more preferably an agent for EOR, further preferably an agent for chemical EOR.
<41>
A surfactant composition comprising the surfactant according to any one of <1> to <40>.
<42>
The surfactant composition according to <41>, wherein a content of the surfactant in the surfactant composition is preferably 0.01 mass % or more, more preferably 0.05 mass % or more, further preferably 0.1 mass % or more, and preferably 15 mass % or less, more preferably 10 mass % or less, further preferably 5 mass % or less.
<43>
The surfactant composition according to <41> or <42>, comprising a solvent.
<44>
The surfactant composition according to <43>, wherein a content of the solvent in the surfactant composition is preferably 30 mass % or less, more preferably 20 mass % or less, further preferably 10 mass % or less, still more preferably 5 mass % or less, still more preferably 1 mass % or less, still more preferably 0 mass %.
<45>
The surfactant composition according to any one of <41> to <44>, being an emulsifier composition, a wetting agent composition, a penetrant composition, a composition for oil recovery, or a detergent composition.
<46>
The surfactant composition according to any one of <41> to <44>, being an emulsifier composition, a wetting agent composition, a penetrant composition, a composition for oil recovery, or a detergent composition containing one or more kinds of the compound represented by the Chemical Formula (1).
<47>
The surfactant composition according to <45> or <46>, wherein the composition for oil recovery is preferably a composition for crude oil recovery, more preferably a composition for EOR, further preferably a composition for chemical EOR.
<48>
An emulsifier, a wetting agent, a penetrant, an agent for oil recovery, or a detergent, comprising one or more kinds of the compound represented by the Chemical Formula (1).
<49>
An emulsifier, a wetting agent, a penetrant, an agent for oil recovery, or a detergent, composed of the compound represented by the Chemical Formula (1).
<50>
An emulsifier, a wetting agent, a penetrant, an agent for oil recovery, or a detergent, composed of one or more kinds of the compound represented by the Chemical Formula (1).
<51>
The agent for oil recovery according to any one of <48> to <50>, being preferably an agent for crude oil recovery, more preferably an agent for EOR, further preferably an agent for chemical EOR.
<52>
An emulsifier composition, a wetting agent composition, a penetrant composition, a composition for oil recovery, or a detergent composition, comprising one or more kinds of the compound represented by the Chemical Formula (1).
<53>
The composition for oil recovery according to <52>, being preferably a composition for crude oil recovery, more preferably a composition for EOR, further preferably a composition for chemical EOR.
<54>
Use of the surfactant according to any one of <1> to <35> as an emulsifier, a wetting agent, a penetrant, an agent for oil recovery, or a detergent.
<55>
Use of the surfactant according to <54>, wherein the agent for oil recovery is preferably an agent for crude oil recovery, more preferably an agent for EOR, further preferably an agent for chemical EOR.
<56>
Use of the surfactant composition according to any one of <41> to <44> as an emulsifier composition, a wetting agent composition, a penetrant composition, a composition for oil recovery, or a detergent composition.
<57>
Use of the surfactant composition according to <56>, wherein the composition for oil recovery is preferably a composition for crude oil recovery, more preferably a composition for EOR, further preferably a composition for chemical EOR.
<58>
Use of one or more kinds of the compound represented by the Chemical Formula (1) as an emulsifier, a wetting agent, a penetrant, an agent for oil recovery, or a detergent.
<59>
Use of one or more kinds of the compound represented by the Chemical Formula (1) according to <58>, wherein the agent for oil recovery is preferably an agent for crude oil recovery, more preferably an agent for EOR, further preferably an agent for chemical EOR.
<60>
Use of a composition comprising one or more kinds of the compound represented by the Chemical Formula (1) as an emulsifier composition, a wetting agent composition, a penetrant composition, a composition for oil recovery, or a detergent composition.

<61>

Use of the composition according to <60>, wherein the composition for oil recovery is preferably a composition for crude oil recovery, more preferably a composition for EOR, further preferably a composition for chemical EOR.

EXAMPLES

Hereinafter, a specific description is made of the present invention with reference to Examples. The content of each component is expressed in mass % unless otherwise indicated in Tables. Various measuring methods are as follows.

Method for Measuring Double Bond Distribution in Olefin

The double bond distribution in olefin was measured by gas chromatography (hereinafter, abbreviated as GC). Specifically, dimethyl disulfide was reacted with olefin to form a dithioated derivative, and then respective components were separated by GC. The double bond distribution in olefin was determined from respective peak areas. The apparatus used for measurement and analyzing conditions are as follows.

GC apparatus: Trade name HP6890 (manufactured by Hewlett-Packard Company)

Column: Trade name Ultra-Alloy-1 HT capillary column 30 m×250 μm×0.15 μm (manufactured by Frontier Laboratories, Ltd.)

Detector: Hydrogen flame ion detector (FID)

Injection temperature: 300° C.

Detector temperature: 350° C.

Oven: 60° C. (0 min.)→2° C./min.→225° C.→20° C./min. 350° C.→350° C. (5.2 min.)

<Method for Measuring Content Ratio of Structural Isomer>

Measurement was performed by $^1$H-NMR for a mixture of 0.05 g of alkyl glyceryl ether, 0.2 g of trifluoroacetic anhydride, and 1 g of deuterated chloroform. Measuring conditions are as follows.

Nuclear magnetic resonance apparatus: Agilent 400-MR DD2, manufactured by Agilent Technologies, Inc.

Observation range: 6410.3 Hz

Data point: 65536

Measurement mode: Presat

Pulse width: 45°

Pulse delay time: 10 sec

Cumulative number: 128 times

<Production of Internal Olefin>

Production Example A1

(Production of internal olefin having 16 carbon atoms (internal olefin 1))

A flask equipped with a stirrer was charged with 7000 g (28.9 mol) of 1-hexadecanol (Product name: KALCOL 6098, manufactured by Kao Corporation) and 700 g (10 wt % with respect to the raw material alcohol) of γ-alumina (STREM Chemicals, Inc.) as a solid acid catalyst, followed by reaction at 280° C. for 32 hours under stirring with circulation of nitrogen (7000 mL/min) in the system. The alcohol conversion after completion of the reaction was 100%, and the purity of C16 olefin was 99.6%. The obtained crude C16 internal olefin was transferred to a distiller, followed by distillation at 136 to 160° C./4.0 mmHg to yield an internal olefin 1 having an olefin purity of 100%. The double bond distribution in the obtained internal olefin 1 was 0.2% at the C1 position, 15.8% at the C2 position, 14.5% at the C3 position, 15.7% at the C4 position, 17.3% at the C5 position, 16.5% at the C6 position, and 20.0% at the C7 position and the C8 position in total.

Production Example A2

(Production of Internal Olefin having 18 Carbon Atoms (Internal Olefin 2))

A reactor equipped with a stirrer was charged with 800 kg (3.0 kmol) of 1-octadecanol (Product name: KALCOL 8098, manufactured by Kao Corporation) and 80 kg (10 wt % with respect to the raw material alcohol) of activated alumina GP-20 (Mizusawa Industrial Chemicals, Ltd.) as a solid acid catalyst, followed by reaction at 280° C. for 16 hours under stirring with circulation of nitrogen (15 L/min) in the system. The alcohol conversion after completion of the reaction was 100%, and the purity of C18 olefin was 98.7%. The obtained crude C18 internal olefin was transferred to a distiller, followed by distillation at 163 to 190° C./4.6 mmHg to yield an internal olefin 2 having an olefin purity of 100%. The double bond distribution in the obtained internal olefin 2 was 0.3% at the C1 position, 13.3% at the C2 position, 12.6% at the C3 position, 13.9% at the C4 position, 14.8% at the C5 position, 13.7% at the C6 position, 12.6% at the C7 position, and 18.8% at the C8 position and the C9 position in total.

Production Example A3

(Production of Internal Olefin having 14 Carbon Atoms (Internal Olefin 3))

An internal olefin 3 was obtained in the same manner as in Production Example A1 except that 28.9 mol of 1-tetradecanol (Product name: KALCOL 4098, manufactured by Kao Corporation) was used in place of 28.9 mol of 1-hexadecanol (Product name: KALCOL 6098, manufactured by Kao Corporation) for Production Example A1. The double bond distribution in the obtained internal olefin 3 was 1.3% at the C1 position, 31.8% at the C2 position, 23.8% at the C3 position, 21.0% at the C4 position, 8.5% at the C5 position, and 13.6% at the C6 position and C7 position in total.

<Production of Internal Epoxide>

Production Example B1

(Production of Internal Epoxide having 16 Carbon Atoms (Internal Epoxide 1))

A flask equipped with a stirrer was charged with the internal olefin 1 (800 g, 3.56 mol) obtained in Production Example A1, 107 g (1.78 mol) of acetic acid (manufactured by Wako Pure Chemical Industries, Ltd.), 15.6 g (0.15 mol) of sulfuric acid (manufactured by Wako Pure Chemical Industries, Ltd.), 415.7 g (4.28 mol) of 35% hydrogen peroxide (manufactured by Wako Pure Chemical Industries, Ltd.), and 25.3 g (0.18 mol) of sodium sulfate (manufactured by Wako Pure Chemical Industries, Ltd.), followed by reaction at 50° C. for 4 hours. Thereafter, the temperature was raised to 70° C. to allow the mixture to react further for 2 hours. After the reaction, the layers were separated to remove an aqueous layer, and an oil layer was washed with ion-exchanged water, a saturated aqueous sodium carbonate solution (manufactured by Wako Pure Chemical Industries, Ltd.), a saturated aqueous sodium sulfite solution (manufactured by Wako Pure Chemical Industries, Ltd.), and 1% saline (manufactured by Wako Pure Chemical Industries, Ltd.), followed by concentration in an evaporator to yield 820 g of an internal epoxide 1.

Production Example B2

(Production of Internal Epoxide having 18 Carbon Atoms (Internal Epoxide 2))

A flask equipped with a stirrer was charged with the internal olefin 2 (595 g, 2.38 mol) obtained in Production Example A2, 71.7 g (1.20 mol) of acetic acid (manufactured by Wako Pure Chemical Industries, Ltd.), 9.8 g (0.10 mol) of sulfuric acid (manufactured by Wako Pure Chemical Industries, Ltd.), and 324 g (4.00 mol) of 35% hydrogen peroxide (manufactured by Wako Pure Chemical Industries, Ltd.), followed by reaction at 50° C. for 4 hours. Thereafter, the temperature was raised to 80° C. to allow the mixture to react further for 5 hours. After the reaction, the layers were separated to remove an aqueous layer, and an oil layer was washed with ion-exchanged water, a saturated aqueous sodium carbonate solution (manufactured by Wako Pure Chemical Industries, Ltd.), a saturated aqueous sodium sulfite solution (manufactured by Wako Pure Chemical Industries, Ltd.), and ion-exchanged water, followed by concentration in an evaporator to yield 629 g of an internal epoxide 2.

Production Example B3

(Production of Internal Epoxide having 14 Carbon Atoms (Internal Epoxide 3))

An internal epoxide 3 was obtained in the same manner as in Production Example B1 except that the internal olefin 3 (3.56 mol) obtained in Production Example A3 was used in place of the internal olefin 1 (3.56 mol) obtained in Production Example A1.

<Production of Reactant of Epoxide and Glycerin (Alkyl Glyceryl ether, AGE)>

Hereinafter, the alkyl glyceryl ether is referred to as AGE. In addition, AGE1, AGE2, AGE3, and the like represent alkyl glyceryl ether 1, alkyl glyceryl ether 2, alkyl glyceryl ether 3, and the like, respectively.

Production Example C1

(Production of Reactant of Internal Epoxide 1 and Glycerin (AGE1))

A flask equipped with a stirrer was charged with 2298 g (25.0 mol) of glycerin (manufactured by Wako Pure Chemical Industries, Ltd.) and 0.122 g (1.25 mmol) of 98% sulfuric acid (manufactured by Wako Pure Chemical Industries, Ltd.), and the temperature was raised to 130° C. Thereafter, the internal epoxide 1 (300 g, 1.25 mol) obtained in Production Example B1 was added dropwise over 1 hour, followed by reaction at 130° C./8 hours. Hexane was added to the liquid obtained by this reaction, followed by washing with ion-exchanged water. Subsequently, concentration was performed under reduced pressure in an evaporator to yield 400 g of AGE1. The obtained AGE1 wherein in the Chemical Formula (1), $R^1$ and $R^2$ each contain an alkyl group having 1 to 13 carbon atoms, the total number of carbon atoms of $R^1$ and $R^2$ is 14, X is a single bond, one of $A^1$ and $A^2$ is —OH and the other is —O—$CH_2$—CH(OH)—$CH_2$OH or —O—CH(—$CH_2$—OH)$_2$, contained 73% ether alcohol 1 (AGE obtained by reacting the hydroxyl group at the 1-position of glycerin with the epoxy group) in which $A^1$ or $A^2$ was —O—$CH_2$—CH(OH)—$CH_2$OH, and 27% ether alcohol 2 (AGE obtained by reacting the hydroxyl group at the 2-position of glycerin with the epoxy group) in which $A^1$ or $A^2$ was —O—CH(—$CH_2$—OH)$_2$.

Production Example C2

(Production of Reactant of Internal Epoxide 2 and Glycerin (AGE2))

An AGE2 was obtained in the same manner as in Production Example C1 except that the internal epoxide 2 (1.25 mol) obtained in Production Example B2 was used in place of the internal epoxide 1 (1.25 mol) obtained in Production Example B1. The obtained AGE2 wherein in the Chemical Formula (1), $R^1$ and $R^2$ each contain an alkyl group having 1 to 15 carbon atoms, the total number of carbon atoms of $R^1$ and $R^2$ is 16, X is a single bond, one of $A^1$ and $A^2$ is —OH and the other is —O—$CH_2$—CH(OH)—$CH_2$OH or —O—CH(—$CH_2$—OH)$_2$, contained 72% AGE obtained by reacting the hydroxyl group at the 1-position of glycerin with the epoxy group, and 28% AGE obtained by reacting the hydroxyl group at the 2-position of glycerin with the epoxy group.

Production Example C3

(Production of Reactant of Internal Epoxide 3 and Glycerin (AGE3))

An AGE3 was obtained in the same manner as in Production Example C1 except that the internal epoxide 3 (1.25 mol) obtained in Production Example B3 was used in place of the internal epoxide 1 (1.25 mol) obtained in Production Example B1. The obtained AGE3 wherein in the Chemical Formula (1), $R^1$ and $R^2$ each contain an alkyl group having 1 to 11 carbon atoms, the total number of carbon atoms of $R^1$ and $R^2$ is 12, X is a single bond, one of $A^1$ and $A^2$ is —OH and the other is —O—$CH_2$—CH(OH)—$CH_2$OH or —O—CH(—$CH_2$—OH)$_2$, contained 74% AGE obtained by reacting the hydroxyl group at the 1-position of glycerin with the epoxy group, and 26% AGE obtained by reacting the hydroxyl group at the 2-position of glycerin with the epoxy group.

Production Example C4

(Production of Reactant of C16 Terminal Epoxide and Glycerin (AGE4))

An AGE4 was obtained in the same manner as in Production Example C1 except that 1.25 mol of a C16 terminal epoxide (manufactured by Tokyo Chemical Industry Co., Ltd.) was used in place of the internal epoxide 1 (1.25 mol) obtained in Production Example B1. The obtained AGE4 wherein in the Chemical Formula (1), $R^1$ is a hydrogen atom, $R^2$ is an alkyl group having 14 carbon atoms, the total number of carbon atoms of $R^1$ and $R^2$ is 14, X is a single bond, one of $A^1$ and $A^2$ is —OH and the other is —O—$CH_2$—CH(OH)—$CH_2$OH or —O—CH(—$CH_2$—OH)$_2$, contained 50% AGE obtained by reacting the hydroxyl group at the 1-position of glycerin with the epoxy group, and 50% AGE obtained by reacting the hydroxyl group at the 2-position of glycerin with the epoxy group.

The following measurement and evaluation were performed using the produced AGEs 1 to 4. Unless otherwise specified, the measurement and evaluation were performed at room temperature (20° C.). In Tables 1 to 5, AGE represents alkyl glyceryl ether.

<Evaluation of Emulsifiability>

Example 1 (Examples 1-1 to 1-9, Comparative Examples 1-1 to 1-4)

In a 50 mL glass sample bottle, 0.5 g of a surfactant described in Table 1, 10 mL of ion-exchanged water, and 10 mL of each of various oils were put, and shaken for 30 seconds. Then, one droplet was placed on a slide glass, covered with a cover glass, and observed at a magnification of 500 times using a digital microscope VHX-6000 (manufactured by KEYENCE CORPORATION). The particle diameters of the droplets were measured and evaluated according to the following criteria. The results are shown in Table 1.
1: Average particle diameter is less than 100 μm
2: Average particle diameter is more than 100 μm
3: Separation occurs and no droplet is observed.
<Evaluation of Wettability>

Example 2 (Examples 2-1 to 2-4, Comparative Examples 2-1 to 2-2)

A polypropylene substrate (80 mm×30 mm×1 mm) was horizontally placed on the stage of a contact angle meter (DM-701 manufactured by Kyowa Interface Science Co., Ltd.), 2 μL of a composition described in Table 2 (a surfactant composition or the like) was dropped onto the placed slide glass with a syringe, and the contact angle was measured after 10 seconds. The results are shown in Table 2.
<Evaluation of Permeability>

Example 3 (Examples 3-1 to 3-3, Comparative Example 3-1)

In a 100 mL beaker, 50 mL of a composition described in Table 3 (a surfactant composition or the like) adjusted to 20° C. was put. On the composition, a cotton canvas cloth (gray fabric, knitting, 2.0×2.0 cm) was gently floated. Then, the time until the cotton canvas cloth started to sink below the water surface was measured. The measurement was performed five times to derive the average value. The results are shown in Table 3.
<Evaluation of Detergency>

Example 4 (Examples 4-1 to 4-2, Comparative Examples 4-1 to 4-2)

Onto a hard polyvinyl chloride resin plate (50 mm×20 mm×2 mm), 80 μL of beef tallow heated to 80° C. and completely dissolved was dropped. Then, the hard polyvinyl chloride resin plate was allowed to stand at room temperature overnight for solidification. This resin plate was immersed in 50 g of a composition (a surfactant composition or the like) described in Table 4 adjusted to 30° C., and the time during which the beef tallow peeled off from the resin plate was measured as a washing time. The results are shown in Table 4.

<Evaluation of Microemulsion forming Ability>

Example 5 (Examples 5-1 to 5-3, Comparative Examples 5-1 to 5-6)

To ion-exchanged water, NaCl (20 mass %) and $CaCl_2$ (6 mass %) were added to prepare a salt aqueous solution.
In a 100 mL screw tube, 80 mL of each of oils described in Table 5 and the salt aqueous solution was put at a volume ratio of 1:1, and further 0.8 mL of each of surfactants described in Table 5 was added. Then, the tube was sealed, and shaken for 30 seconds. After standing at 80° C. for 3 days, the volume and appearance of the aqueous phase were observed.
The microemulsion forming ability was evaluated as follows: in a case where the volume of the aqueous phase in the lower part was 55% or more, and the aqueous phase was not cloudy, the case was determined that "there is microemulsion formation", and the other cases were determined that "there is no microemulsion formation". The results are shown in Table 5. Comparative products 1 to 3 shown in Table 5 are as follows.
Comparative Product 1: 2-ethylhexylglyceryl ether (2-ethylhexyl glyceryl ether can be produced, for example, by the method described in paragraphs [0002] and [0003] of JP-A-2008-156289.)
Comparative Product 2: polyoxyethylene (3) lauryl ether (EMULGEN 103, manufactured by Kao Corporation)
Comparative Product 3: alkyl glucoside (MYDOL 12, manufactured by Kao Corporation)

TABLE 1

|  | Surfactant | Oil | Evaluation of Emulsifiability |
|---|---|---|---|
| Example 1-1 | AGE 1 | Decane | 1 |
| Example 1-2 |  | Toluene | 1 |
| Example 1-3 |  | Triolein | 2 |
| Example 1-4 | AGE 2 | Decane | 1 |
| Example 1-5 |  | Toluene | 1 |
| Example 1-6 |  | Oleic Acid | 1 |
| Example 1-7 |  | Triolein | 1 |
| Example 1-8 | AGE 3 | Decane | 1 |
| Example 1-9 |  | Oleic Acid | 1 |
| Comparative Example 1-1 | — | Decane | 3 |
| Comparative Example 1-2 | — | Toluene | 3 |
| Comparative Example 1-3 | — | Oleic Acid | 3 |
| Comparative Example 1-4 | — | Triolein | 3 |

TABLE 2

|  | Surfactant | | Blending Amount (Mass%) of Each Component in Composition | | | | Contact Angle (°) |
|---|---|---|---|---|---|---|---|
|  | Kind | Position of Glyceryl Ether Group | Surfactant | Diethylene Glycol Monobutyl Ether | Ion Exchanged Water | Total | |
| Example 2-1 | AGE1 | Internal | 1 | 20 | Balance | 100 | 24 |
| Example 2-2 | AGE2 | Internal | 1 | 20 | Balance | 100 | 24 |
| Example 2-3 | AGE3 | Internal | 1 | 20 | Balance | 100 | 20 |
| Example 2-4 | AGE4 | Terminal | 1 | 20 | Balance | 100 | 22 |
| Comparative Example 2-1 | — | — | 0 | 0 | Balance | 100 | 97 |
| Comparative Example 2-2 | — | — | 0 | 20 | Balance | 100 | 41 |

TABLE 3

| | Surfactant | Blending Amount (Mass %) of Each Component in Composition Surfactant | Ion Exchanged Water | Total | Time to Start to Sink (s) |
|---|---|---|---|---|---|
| Example 3-1 | AGE 1 | 0.1 | Balance | 100 | 25 |
| Example 3-2 | AGE 2 | 0.1 | Balance | 100 | 44 |
| Example 3-3 | AGE 3 | 0.1 | Balance | 100 | 10 |
| Comparative Example 3-1 | — | 0 | Balance | 100 | >600 |

TABLE 4

| | Surfactant | Blending Amount (Mass %) of Each Component in Composition Surfactant | Diethylene Glycol Monobutyl Ether | Ion Exchanged Water | Total | Washing Time (h) |
|---|---|---|---|---|---|---|
| Example 4-1 | AGE1 | 3 | 16 | Balance | 100 | 1 |
| Example 4-2 | AGE2 | 3 | 16 | Balance | 100 | 1 |
| Comparative Example 4-1 | — | 0 | 0 | Balance | 100 | >72 |
| Comparative Example 4-1 | — | 0 | 16 | Balance | 100 | >72 |

| | Example 5-1 | Example 5-2 | Example 5-3 | Comparative Example 5-1 | Comparative Example 5-2 | Comparative Example 5-3 | Comparative Example 5-4 | Comparative Example 5-5 | Comparative Example 5-6 |
|---|---|---|---|---|---|---|---|---|---|
| Surfactant | AGE2 | AGE1 | AGE3 | — | Comparative Product 1 | Comparative Product 2 | Comparative Product 3 | — | — |
| Oil | Octane | Octane | Octane | Octane | Octane | Octane | Octane | Toluene | Hexadecane |
| Volume of Aqueous Phase after Standing at 80° C. for 3 Days [%] | 65 | 64 | 64 | 50 | 49 | 49 | 51 | 50 | 50 |
| Appearance of Aqueous Phase after Standing at 80° C. for 3 Days | Slight Cloudiness | Slight Cloudiness | Slight Cloudiness | Transparent | Transparent | Transparent | Transparent | Transparent | Transparent |
| Formation of Microemulsion | Yes | Yes | Yes | No | No | No | No | No | No |

INDUSTRIAL APPLICABILITY

The surfactant and the surfactant composition of the present invention are useful as, for example, a detergent such as a liquid detergent for clothing, a detergent for dishware, a detergent for hair, a detergent for body, a detergent for precision parts, and a detergent for hard surfaces.

The invention claimed is:

1. A surfactant comprising at least one kind of a compound represented by a Chemical Formula (1):

[Chemical Formula (1)]

wherein $R^1$ is a hydrogen atom or an aliphatic hydrocarbon group having 1 or more and 33 or less carbon atoms, $R^2$ is an aliphatic hydrocarbon group having 1 or more and 33 or less carbon atoms, a total number of carbon atoms of $R^1$ and $R^2$ is 1 or more and 34 or less, X is a single bond or an aliphatic hydrocarbon group having 1 or more and 5 or less carbon atoms, and one of $A^1$ and $A^2$ is —OH and the other is —O—$CH_2$—CH(OH)—$CH_2$OH or —O—CH(—$CH_2$—OH)$_2$.

2. The surfactant according to claim 1, wherein in the compound represented by the Chemical Formula (1), X is a single bond.

3. The surfactant according to claim 1, wherein in the compound represented by the Chemical Formula (1), $R^1$ is an aliphatic hydrocarbon group having 1 or more and 33 or less carbon atoms.

4. The surfactant according to claim 1, comprising a compound 1 in which in the Chemical Formula (1), one of $A^1$ and $A^2$ is —OH and the other is —O—$CH_2$—CH(OH)—$CH_2$OH, and a compound 2 in which in the Chemical Formula (1), one of $A^1$ and $A^2$ is —OH and the other is —O—CH(—$CH_2$—OH)$_2$.

5. The surfactant according to claim 1, comprising in the compound represented by the Chemical Formula (1), two or more kinds of the compound between which total numbers of carbon atoms of $R^1$ and $R^2$ are the same, but numbers of carbon atoms of $R^1$ and numbers of carbon atoms of $R^2$ are each different.

6. A surfactant composition comprising the surfactant according to claim 1.

7. The surfactant according to claim 1, being an agent for oil recovery.

8. The surfactant composition according to claim 6, being a composition for oil recovery.

9. The surfactant according to claim 2, wherein in the compound represented by the Chemical Formula (1), $R^1$ is an aliphatic hydrocarbon group having 1 or more and 33 or less carbon atoms.

10. The surfactant according to claim 2, comprising a compound 1 in which in the Chemical Formula (1), one of $A^1$ and $A^2$ is —OH and the other is —O—$CH_2$—CH(OH)—$CH_2$OH, and a compound 2 in which in the Chemical Formula (1), one of $A^1$ and $A^2$ is —OH and the other is —O—CH(—$CH_2$—OH)$_2$.

11. The surfactant according to claim 3, comprising a compound 1 in which in the Chemical Formula (1), one of $A^1$ and $A^2$ is —OH and the other is —O—$CH_2$—CH(OH)—$CH_2$OH, and a compound 2 in which in the Chemical Formula (1), one of $A^1$ and $A^2$ is —OH and the other is —O—CH(—$CH_2$—OH)$_2$.

12. The surfactant according to claim 2, comprising in the compound represented by the Chemical Formula (1), two or more kinds of the compound between which total numbers of carbon atoms of $R^1$ and $R^2$ are the same, but numbers of carbon atoms of $R^1$ and numbers of carbon atoms of $R^2$ are each different.

13. The surfactant according to claim 3, comprising in the compound represented by the Chemical Formula (1), two or more kinds of the compound between which total numbers of carbon atoms of $R^1$ and $R^2$ are the same, but numbers of carbon atoms of $R^1$ and numbers of carbon atoms of $R^2$ are each different.

14. The surfactant according to claim 4, comprising in the compound represented by the Chemical Formula (1), two or more kinds of the compound between which total numbers of carbon atoms of $R^1$ and $R^2$ are the same, but numbers of carbon atoms of $R^1$ and numbers of carbon atoms of $R^2$ are each different.

15. A surfactant composition comprising the surfactant according to claim 2.

16. A surfactant composition comprising the surfactant according to claim 3.

17. A surfactant composition comprising the surfactant according to claim 4.

18. A surfactant composition comprising the surfactant according to claim 5.

19. The surfactant according to claim 2, being an agent for oil recovery.

20. The surfactant according to claim 3, being an agent for oil recovery.

* * * * *